United States Patent [19]

Muraoka et al.

[11] Patent Number: 6,130,338
[45] Date of Patent: Oct. 10, 2000

[54] METHOD OF PRODUCING PYRROLIDINE DERIVATIVES

[75] Inventors: Hideo Muraoka; Haruyo Sato, both of Nagoya, Japan

[73] Assignee: Toray Industries, Inc., Japan

[21] Appl. No.: 09/390,160

[22] Filed: Sep. 3, 1999

[30] Foreign Application Priority Data

Sep. 8, 1998 [JP] Japan .................................. 10-254304
Nov. 30, 1998 [JP] Japan .................................. 10-339893

[51] Int. Cl.$^7$ .................................................. C07D 487/06
[52] U.S. Cl. ............................................................. 548/453
[58] Field of Search ............................................. 548/453

[56] References Cited

U.S. PATENT DOCUMENTS

| 3,657,274 | 4/1972 | Ohki et al. ........................... 260/326.3 |
| 3,691,198 | 9/1972 | Brown et al. ........................ 260/326.8 |
| 4,175,099 | 11/1979 | Giessler . |
| 4,230,718 | 10/1980 | Walsh et al. ............................ 424/274 |
| 5,453,560 | 9/1995 | Kulprathipanja . |

FOREIGN PATENT DOCUMENTS

| 0046068 | 2/1982 | European Pat. Off. . |
| 0125077 | 11/1984 | European Pat. Off. . |
| 49-102624 | 9/1974 | Japan . |
| 06239808 | 8/1994 | Japan . |

OTHER PUBLICATIONS

A Facile Synthesis of 3–Pyrrolines, Zhaozhong Ding and Joseph J. Tufariello, *Synthetic Communications*, 20(2), 227–230 (1990).

Regio– and Stereoselective Functionalization Of An Optically Active Tetrahydroindolizine Derivative. Catalytic Asymmetric Syntheses of Lentiginosine, 1,2–Diepilentiginosine, and Gephyrotoxin 209D, Seiji Nukui, Mikiko Sodeoka, Hiroaki Sasai and Masakatsu Shibasaki, *J. Org. Chem.*, 1995, 60, 398–404.

Use of Dioxiranes for the Chemoselective Oxidation of Tertiary Amines Bearing Alkene Moieties, Marta Ferrer, Francisco Sánchez–Baeza, Angel Messeguer, Anna Diez and Mario Rubiralta, *J. Chem. Soc., Chem. Commun.*, 1995.

Epoxidation of an Unsaturated Tertiary Amine. Application to the Synthesis of Two Pirprofen Metabolites, Naba K. Chaudhuri and Thomas J. Ball, *J. Org. Chem.*, 1982, 47, 5196–5198.

*Primary Examiner*—Joseph McKane
*Assistant Examiner*—Dominic Keating
*Attorney, Agent, or Firm*—Austin R. Miller

[57] ABSTRACT

A method for producing pyrrolidine derivatives such as 3,4-epoxypyrrolodines, 3-pyrrolidols and the like, by oxidizing 3-pyrrolines with at least one peroxide in the presence of at least one acid is disclosed. The 3-pyrrolines are produced by deriving cis-2-butene compounds from cis-2-butene-1,4-diols and performing a cyclization between the cis-2-butene derivatives and at least one primary amine. The method may be performed as a one-pot synthesis and may be performed as a continuous reaction.

3 Claims, No Drawings

METHOD OF PRODUCING PYRROLIDINE DERIVATIVES

BACKGROUND OF THE INVENTION

1. Field of the Invention

The present invention relates to methods of producing pyrrolidine derivatives. The purpose of the invention is to provide simple and efficient industrial production of pyrrolidine derivatives such as epoxypyrrolidines, pyrrolidinols, and the like. These pyrrolidine derivatives are important and useful synthetic intermediates for pharmaceuticals, and can be transformed to several kinds of pyrrolidine derivatives.

2. Description of the Prior Art

There are a few examples of forming 3,4-epoxypyrrolidines having formula (2) by epoxidizing the C=C double bond in 3-pyrrolines having formula (3). U.S. Pat. No. 3,657,274 discloses the use of trifluoroperacetic acid; Tetrahedron Letters 36, 1621 (1995) and Tetrahedron Letters 39, 8885 (1998), J. Org. Chem. 60, 398 (1995) disclose the use of m-CPBA (m-chloroperbenzoic acid) and Tetrahedron Letters 37, 3255 (1996) discloses the use of dioxiranes. All of these methods have the following problems: (1) highly dangerous peroxides are used in the reaction, (2) the processes of producing these peroxides are very complex and involve reagents which are hard to use in the industrial methods (e.g. 90% $H_2O_2$), (3) in the group at the 1-position of 3-pyrrolines having formula (3), $R^1$, is limited to the less basic compounds (such as amides, carbamates, and sulfamides) than ordinary cyclic amines (such as t-butoxycarbonyl (Boc), benzyloxycarbonyl (Cbz), p-toluenesulfonyl (Ts), and benzoyl (Bz) groups). This is why by-products of 3-pyrroline N-oxides are obtained selectively from ordinary cyclic amines with arakyl, aryl, and/or alalkyl groups at the 1-position of 3-pyrrolines.

On the other hand, there are a few examples in which epoxidation of basic 3-pyrrolines is disclosed. U.S. Pat. No. 4,230,718 discloses the formation of 3,4-epoxypyrrolidines via chlorohydrins, from 3-pyrrolines using aqueous HCl and $Cl_2$ gas. Epoxidation of 3-pyrrolines using $CH_3CN$ and $H_2O_2$ is disclosed in J. Org. Chem. 47, 5196 (1982), and J. Chem. Soc., Chem. Commun. 293 (1995) discloses the use of $BF_3/OEt_2$. Unfortunately, 3,4-dichloropyrrolidine by-products are formed in U.S. Pat. No. 4,230,718, and pyrrole by-products are formed in J. Org. Chem. 47, 5196 (1982). In the case of J. Chem. Soc., Chem. Commun. 293 (1995), both $BF_3/OEt_2$ and dioxiranes are expensive and are difficult to use from the point of industrialization.

Therefore, these kinds of the oxidation reactions without limitation of substituents on nitrogen, and without production of by-products are unknown. Needless to say, nothing in the above reactions is useful for persulfates to be accelerated by irradiation.

Examples of the synthesis of 3-pyrrolidinols having formula (1) from 3,4-epoxypyrrolidines having formula (2) are found in Tetrahedron Letters 35, 7099 (1994), Tetrahedron Letters 39, 8885 (1998), J. Org. Chem 47, 5196 (1982), J. Org. Chem 60, 398 (1995) (by hydrolysis), and in U.S. Pat. No. 4,254,135 and German Patent No. 3,906,365 (by alcoholysis and aminolysis). These methods have the following disadvantages: (1) the synthesized 3,4-epoxypyrrolidines must be subjected to several isolation processes including distillation, crystallization, etc. to derivatize 3-pyrrolidinols, (2) total yields are low, (3) operation is inconvenient and costs are high.

(4) There is no known one-pot synthesis of 3-pyrrolidinols having formula (1) from 3-pyrrolines having formula (3).

One-pot synthesis of 3,4-dihydroxypyrrolidines from 3-pyrroline compounds is disclosed by J. Org. Chem. 60, 398 (1995), Tetrahedron Letters 35, 7099 (1998), and Tetrahedron Letters 28, 535 (1987) in which N-methylmorpholine N-oxides are used in the presence of osmium tetroxide ($OsO_4$) or potassium permanganate ($KMnO_4$). However, these methods have the following problems: (1) they are only available for the synthesis of cis-3,4-dihydroxypyrrolidines, (2) waste liquid, including oxidizing reagents of osmium tetroxide ($OsO_4$) and potassium permanganate ($KMnO_4$) can cause problems under certain circumstances.

There are a few examples of the synthesis of 3-pyrrolines having formula (3) with cyclization between cis-2-butene derivatives having formula (7) and primary amines having formula (8). In U.S. Pat. No. 3,657,274 cis-1,4-dichloro-2-butene ($R^8=R^9=H$; $A^1=A^2=Cl$) is used as a starting material. In Syn. Commun. 20, 227 (1990), cis-2-butene-1,4-diol dimethanesulfonylate ($R^8=R^9=H$, $A^1=A^2=OSO_2CH_3$) is used as starting material. These methods have the following problems: (1) cis-1,4-dichloro-2-butene ($R^8=R^9=H$; $A^1=A^2=Cl$) is not only hard to produce industrially at low cost, but it is also a carcinogen, (2) cis-2-butene-1,4-diol dimethanesulfonylate ($R^8=R^9=H$; $A^1=A^2=OSO_2CH_3$) is unstable in the air and decomposes metals.

SUMMARY OF THE INVENTION

The present invention provides a novel method of preparing pyrrolidine derivatives such as 3,4-epoxypyrrolidines, 3-pyrrolidinols, and the like, in a novel, simple and efficient procedure.

The invention provides a one-pot synthesis of pyrrolidine derivatives such as 3,4-epoxypyrrolidines, 3-pyrrolidinols from 3-pyrrolines by oxidation with a peroxide in the presence of an acid. These pyrrolidine compounds are important and useful synthetic intermediates for synthesis of pharmaceuticals, and can be transformed into several kinds of pyrrolidine derivatives.

DETAILED DESCRIPTION OF THE INVENTION

The invention provides a method for preparing pyrrolidine derivatives such as 3,4-epoxypyrrolidines, 3-pyrrolidinols and the like, by reacting 3-pyrrolines with at least one peroxide in the presence of at least one acid. Oxidation of the 3-pyrrolines having formula (3) may be accelerated using ultraviolet irradiation, if desired.

The 3-pyrrolidinols are of formula (1):

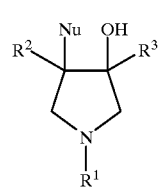

(1)

wherein $R^1$ is hydrogen (H), a halogen, a cyano group (CN), a nitro group ($NO_2$), a hydroxyl group (OH), an alkoxyl group (OR), a carboxyl group ($CO_2H$), an alkoxycarbonyl group ($CO_2R$), an acyl group (COR), a carbamoyl group ($H_2NCO$), a sulfide group (SH, or SR), a sulfinyl group (SOR), a sulfonyl group ($SO_2R$), a sulfamide group ($SO_2NRR'$), or a $C_1$–$C_{10}$ alkyl group, cycloalkyl group, aryl group, aralkyl group which can be optionally substituted, $R^2$ and $R^3$ represent a $C_1$–$C_{10}$ alkyl group, cycloalkyl group, aryl group, alalkyl group which can be optionally substituted, and Nu is a hydroxyl group (OH), an alkoxyl group (OR), or an amino group (NRR') which can be optionally substituted. Optionally, there may be functional groups on the nitrogen atom and/or pyrrolidine ring.

The 3-pyrrolidinols include, but are not limited to, 3,4-dihydroxypyrrolidines, such as 3,4-dihydroxypyrrolidine, 1-methyl-3,4-dihydroxypyrrolidine, 1-cyclohexyl-3,4-dihydroxypyrrolidine, 1-benzyl-3,4-dihydroxypyrrolidine, 1-phenyl-3,4-dihydroxypyrrolidine, 2-[3-chloro-4-(3,4-dihydroxypyrrolidin-1-yl)phenyl]propionic acid, methyl 2-[3-chloro-4-(3,4-dihydroxypyrrolidin-1-yl)phenyl] propionate, and the like.

Specific examples of 3-pyrrolidinols include, but are not limited to, 4-amino-3-pyrrolidinols such as 4-amino-3-pyrrolidinol, 1-methyl-4-amino-3-pyrrolidinol, 1-cyclohexyl-4amino-3-pyrrolidinol, 1-benzyl-4-amino-3-pyrrolidinol, 1-phenyl-4-amino-3-pyrrolidinol, 2-[3-chloro-4-(4-amino-3-hydroxypyrrolidin-1-yl)phenyl]propionic acid, methyl 2-[3-chloro-4-(4-amino-3-hydroxypyrrolidin-1-yl)phenyl]propionate; 4-benzylamino-3-pyrrolidinols such as 4-benzylamino-3-pyrrolidinol, 1-methyl-4-benzylamino-3-pyrrolidinol, 1-cyclohexyl-4-benzylamino-3-pyrrolidinol, 1-benzyl-4-benzylamino-3-pyrrolidinol, 1-phenyl-4-benzylamino-3-pyrrolidinol, 2-[3-chloro-4-(4-benzylamino-3-hydroxypyrrolidin-1-yl)phenyl]propionic acid, methyl 2-[3-chloro-4-(4-benzylamino-3-hydroxypyrrolidin-1-yl)phenyl]propionate, and the like; 4-alkoxy-3-pyrrolidinols such as 4-methoxy-3-pyrrolidinol, 1-methyl-4-methoxy-3-pyrrolidinol, 1-cyclohexyl-4-methoxy-3-pyrrolidinol, 1-benzyl-4-methoxy-3-pyrrolidinol, 1-phenyl-4-methoxy-3-pyrrolidinol, 2-[3-chloro-4-(4-methoxy-3-hydroxypyrrolidin-1-yl)phenyl] propionic acid, methyl 2-[3-chloro-4-(4-methoxy-3-hydroxypyrrolidin-1-yl)phenyl]propionate, and the like.

The 3,4-epoxypyrrolidines are of the formula (2):

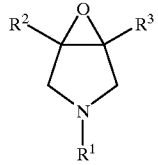

(2)

wherein $R^1$ is hydrogen (H), a halogen, a cyano group (CN), a nitro group ($NO_2$), a hydroxyl group (OH), an alkoxyl group (OR), a carboxyl group ($CO_2H$), an alkoxycarbonyl group ($CO_2R$), an acyl group (COR), a carbamoyl group ($H_2NCO$), a sulfide group (SH, or SR), a sulfinyl group (SOR), a sulfonyl group ($SO_2R$), a sulfamide group ($SO_2NRR'$), or a $C_1$–$C_{10}$ alkyl group, cycloalkyl group, aryl group, aralkyl group which can be optionally substituted; $R^2$ and $R^3$ each represent a $C_1$–$C_{10}$ alkyl group, cycloalkyl group, aryl group, aralkyl group which can be optionally substituted. Optionally, there may be functional groups on the nitrogen atom and/or pyrrolidine ring.

The 3,4-epoxypyrrolidines include, but are not limited to 3,4-epoxypyrrolidine, 1-methyl-3,4-epoxypyrrolidine, 1-cyclohexyl-3,4-epoxypyrrolidine, 1-benzyl-3,4-epoxypyrrolidine, 1-phenyl-3,4-epoxypyrrolidine, 2-[3-chloro-4-(3,4-epoxypyrrolidin-1-yl)phenyl]propionic acid, methyl 2-[3-chloro-4-(3,4-epoxypyrrolidin-1-yl)phenyl] propionate, and the like.

The 3-pyrrolines are of formula (3):

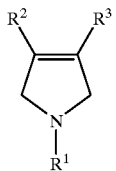

(3)

wherein $R^1$ is hydrogen (H), a halogen, a cyano group (CN), a nitro group ($NO_2$), a hydroxyl group (OH), an alkoxyl group (OR), a carboxyl group ($CO_2H$), an alkoxycarbonyl group ($CO_2R$), an acyl group (COR), a carbamoyl group ($H_2NCO$), a sulfide group (SH, or SR), a sulfinyl group (SOR), a sulfonyl group ($SO_2R$), a sulfamide group ($SO_2NRR'$), or a $C_1$–$C_{10}$ alkyl group, cycloalkyl group, aryl group, aralkyl group which can be optionally substituted; $R^2$ and $R^3$ each represent a $C_1$–$C_{10}$ alkyl group, cycloalkyl group, aryl group, aralkyl group which can be optionally substituted. Optionally, there may be functional groups on the nitrogen atom and/or pyrrolidine ring. The 3-pyrrolines include, but are not limited to 3-pyrroline, 1-methyl-3-pyrroline, 1-ethyl-3-pyrroline, 1-propyl-3-pyrroline, 1-cyclohexyl-3-pyrroline, 1-trichloromethyl-3-pyrroline, 1-phenyl-3-pyrroline, 1-tolyl-3-pyrroline, 1-benzyl-3-pyrroline, 2-[3-chloro-4-(3-pyrrolin-1-yl)phenyl]propionic acid, methyl 2-[3-chloro-4-(3-pyrrolin-1-yl)phenyl] propionate, and the like. Of these compounds, 3-pyrroline, 1-benzyl-3-pyrroline, 1-cyclohexyl-3-pyrroline are preferred. Most preferred are 1-benzyl-3-pyrroline and 1-cyclohexyl-3-pyrroline.

Preferable acids in the oxidation process of 3-pyrrolines are compounds whose formula contains a sulfur atom (S), such as sulfuric acid or sulfonic acids having formula (11). Formula (11) is represented by:

$$R^{14}SO_3H \qquad (11)$$

wherein $R^{14}$ represents a $C_1$–$C_{10}$ alkyl group, cycloalkyl group, aryl group, alalkyl group which can be optionally substituted by a halogen, a cyano group (CN), a nitro group ($NO_2$), a hydroxyl group (OH), an alkoxyl group (OR), a silyl group ($SiR_3$), a carboxyl group ($CO_2H$), an alkoxycarbonyl group ($CO_2R$), and/or an acyl group (COR).

These sulfonic acids having formula (11) can be classified under four sulfonic acids: alkylsulfonic acids, cycloalkyl-sulfonic acids, arylsulfonic acids, and alalkylsulfonic acids. Suitable alkylsulfonic acids include, but are not limited to methanesulfonic acids, trifluoromethanesulfonic acids, trichloromethanesulfonic acids, ethanesulfonic acids, and the like. Suitable cycloalkylsulfonic acids include, but are not limited to, cyclopropanesulfonic acids, cyclohexane-sulfonic acids, and the like. Suitable arylsulfonic acids include, but are not limited to, benzenesulfonic acids, o-, m-, p-fluorobenzenesulfonic acids, o-, m-, p-chlorobenzenesulfonic acids, o-, m-, p-nitrobenzenesulfonic acids, o-, m-, p-cyanobenzenesulfonic acids, o-, m-, p-toluenesulfonic acids, mesitylenesulfonic acids, naphthaleneulfonic acids, and the like. Suitable aralkylsulfonic acids include, but are not limited to, benzylsulfonic acids, o-, m-, p-fluorobenzylsulfonic acids, o-, m-, p-chlorobenzylsulfonic acids, o-, m-, p-nitrobenzylsulfonic acids, o-, m-, p-cyanobenzylsulfonic acids, and the like.

Of these compounds, sulfuric acid, methanesulfonic acids, benzenesulfonic acids, p-chlorobenzenesulfonic acids are preferred. In particular, sulfuric acid is most preferably used.

The preferable amount of acid used is in the range of about 1.0–3.0 mole acid to about 1.0 moles 3-pyrrolines having formula (3) can be used efficiently and economically. Peroxides used in the oxidation of the 3-pyrrolines of formula (3) may be peroxymonosulfuric acids, or their salts (peroxymonosulfates) having formula (4), peroxydisulfuric acids, or their salts (peroxydisulfates) having formula (5). Formula (4) is represented by:

$$M_xH_y(SO_5)_z \qquad (4)$$

wherein M is an alkali metal (1A in the periodic table), an alkaline earth metal (2A in the periodic table), an element from 3A in the periodic table, or an ammonium group having formula (6), and each of x, y, and z can be represented numerically (0–3) provided the relation x+y=2z is satisfied. Formula (5) is represented by:

$$M_xH_y(S_2O_8)_z \qquad (5)$$

where M is an alkali metal (1A in the periodic table), an alkaline earth metal (2A in the periodic table), an element from 3A in the periodic table, or an ammonium group having formula (6), and each of x, y, and z can be represented numerically (0–3) provided the relation x+y=2z is satisfied. Formula (6) is represented by:

$$\begin{array}{c} R^4 \\ | \\ R^5\!\!-\!\!N\!\!-\!\!R^7 \\ | \\ R^6 \end{array} \qquad (6)$$

wherein $R^4$–$R^7$ represent hydrogen, a $C_1$–$C_{20}$ alkyl group, a cycloalkyl group, an aryl group, or an aralkyl group. Peroxymonosulfuric acid, salts (peroxymonosulfates) or peroxydisulfuric acid, salts (peroxydisulfates) are preferable.

Metal peroxymonosulfates include, but are not limited to, sodium peroxymonosulfate ($Na_2SO_5$), potassium peroxymonosulfate ($K_2SO_5$), barium peroxymonosulfate ($BaSO_5$), rubidium peroxymonosulfate ($RbSO_5$), and the like.

Metal peroxyhydrogenmonosulfates include, but are not limited to, sodium peroxyhydrogenmonosulfate ($NaHSO_5$), potassium peroxyhydrogenmonosulfate ($KHSO_5$), and the like.

Ammonium peroxymonosulfates include, but are not limited to, ammonium peroxymonosulfate (($NH_4)_2SO_5$), tetramethylammonium peroxymonosulfate (($Me_4N)_2SO_5$), tetraethylammonium peroxymonosulfate (($Et_4N)_2SO_5$), tetrapropylammonium peroxymonosulfate (($Pr_4N)_2SO_5$), tetrabutylammonium peroxymonosulfate (($Bu_4N)_2SO_5$), tetrahexylammonium peroxymonosulfate, tetradecylammonium peroxymonosulfate, tetralaurylammonium peroxymonosulfate, tetrabenzylammonium peroxymonosulfate (($Bn_4N)_2SO_5$), benzyltrimethylammonium peroxymonosulfate (($BnMe_3N)_2SO_5$), benzyltriethylammonium peroxymonosulfate (($BnEt_3N)_2SO_5$), benzyltributylammonium peroxymonosulfate (($BnBu_3N)_2SO_5$), lauryltrimethylammonium peroxymonosulfate, lauryltriethylammonium peroxymonosulfate, and the like.

Ammonium peroxyhydrogenmonosulfates include, but are not limited to, ammonium peroxyhydrogenmonosulfate (($NH_4)HSO_5$), tetramethylammonium peroxyhydrogenmonosulfate (($Me_4N)HSO_5$), tetraethylammonium peroxyhydrogenmonosulfate (($Et_4N)HSO_5$), tetrapropylammonium peroxyhydrogenmonosulfate (($Pr_4N)HSO_5$), tetrabutylammonium peroxyhydrogemnonosulfate (($Bu_4N)HSO_5$), tetrahexylammonium peroxyhydrogenmonosulfate, tetradecylammonium peroxyhydrogenmonosulfate, tetralaurylammonium peroxyhydrogenmonosulfate, tetrabenzylammonium peroxyhydrogenmonosulfate (($Bn_4N)HSO_5$), benzyltrimethylammonium peroxyhydrogenmonosulfate (($BnMe_3N)HSO_5$), benzyltriethylammonium peroxyhydrogenmonosulfate (($Bnet_3N)HSO_5$), benzyltributylammonium peroxyhydrogenmonosulfate (($BnBu_3N)HSO_5$), lauryltrimethylammonium peroxyhydrogenmonosulfate, lauryltriethylammonium peroxyhydrogenmonosulfate, and the like.

Metal peroxydisulfates include, but are not limited to, sodium peroxydisulfate ($Na_2S_2O_8$), potassium peroxydisulfate ($K_2S_2O_8$), barium peroxydisulfate ($BaS_2O_8$), rubidium peroxydisulfate ($RbS_2O_8$), and the like.

Metal peroxyhydrogenmonosulfates include, but are not limited to, sodium peroxyhydrogenmonosulfate ($NaHS_2O_8$), potassium peroxyhydrogenmonosulfate ($KHS_2O_8$), and the like.

Ammonium peroxydisulfates include, but are not limited to, ammonium peroxydisulfate (($NH_4)_2S_2O_8$), tetramethylammonium peroxydisulfate (($Me_4N)_2S_2O_8$), tetraethylammonium peroxydisulfate (($Et_4N)_2S_2O_8$), tetrapropylammonium peroxydisulfate (($Pr_4N)_2S_2O_8$), tetrabutylammonium peroxydisulfate (($Bu_4N)_2S_2O_8$), tetrahexylammonium peroxydisulfate, tetradecylammonium peroxydisulfate, tetralaurylammonium peroxydisulfate, tetrabenzylammonium peroxydisulfate (($Bn_4N)_2S_2O_8$), benzyltrimethylammonium peroxydisulfate (($BnMe_3N)_2SO_5$), benzyltriethylammonium peroxydisulfate (($BnEt_3N)_2S_2O_8$), benzyltributylammonium peroxydisulfate (($BnBu_3N)_2S_2O_8$), lauryltrimethylammonium peroxydisulfate, lauryltriethylammonium peroxydisulfate, and the like.

Ammonium peroxyhydrogenmonosulfates include, but are not limited to, ammonium peroxyhydrogenmonosulfate (($NH_4)HS_2O_8$), tetramethylamrnonium peroxyhydrogenmonosulfate (($Me_4N)HS_2O_8$), tetraethylammonium peroxyhydrogenmonosulfate (($Et_4N)HS_2O_8$), tetrapropylammonium peroxyhydrogenmonosulfate (($Pr_4N)HS_2O_8$), tetrabutylammonium peroxyhydrogenmonosulfate (($Bu_4N)HS_2O_8$), tetrahexylammonium peroxyhydrogenmonosulfate, tetradecylammonium peroxyhydrogenmonosulfate, tetralaurylammonium peroxyhydrogenmonosulfate, tetrabenzylammonium peroxyhydrogenmonosulfate (($Bn_4N)HS_2O_8$), benzyltrimethylammonium peroxyhydrogenmonosulfate (($BnMe_3N)HS_2O_8$), benzyltriethylammonium peroxyhydrogenmonosulfate (($BnEt_3N)HS_2O_8$), benzyltributylammonium peroxyhydrogenmonosulfate (($BnBu_3N)HS_2O_8$), lauryltrimethylammonium peroxyhydrogenmonosulfate, lauryltriethylammonium peroxyhydrogenmonosulfate, and the like.

The preferable peroxymonosulfate is potassium peroxyhydrogenmonosulfate ($KHSO_5$) Sodium peroxydisulfate ($Na_2S_2O_8$) and/or ammonium peroxydisulfate (($NH_4)_2S_2O_8$) are the preferred peroxydisulfates. The oxidation can be performed either with peroxysulfates alone or with a peroxysulfate mixture. For example, suitable peroxides include OXONE (produced by DuPont), which is a mixture of $KHSO_5/KHSO_4/K_2SO_4=2/1/1$, stabilized by mixing inorganic compounds deactivated for explosion. Suitable amounts of peroxides are in the range of about 1.0–2.0 moles of peroxides to 1.0 mole of 3-pyrrolines having formula (3) and can be preferably used efficiently and economically.

The substituent group Nu in formula (1) derives from nucleophiles of water, alcohols, amines, and the like. Alcohols include, but are not limited to, methanol (MeOH), ethanol (EtOH), propanol (PrOH), butanol (BuOH), hexanol, cyclohexanol, phenol (PhOH), chlorophenol, dichlorophenol, trichlorophenol, catechol, ethylene glycol, diethylene glycol, and the like.

Amines include, but are not limited to, ammonia ($NH_3$), methylamine ($MeNH_2$), ethylamine ($EtNH_2$), propylamine ($PrNH_2$), butylamine ($BuNH_2$), cyclohexylamine, allylamine, homoallylamine, benzylamine ($BnNH_2$), aniline ($PhNH_2$), chloroaniline, bromoaniline, o-, m-, p-toluidine, dimethylamine ($Me_2NH$), diethylamine ($Et_2NH$), dipropylamine ($Pr_2NH$), dibutylamine ($Bu_2NH$), dicyclohexylamine, diallylamine, bis(homoallyl)amine, dibenzylamine ($Bn_2NH$), N-methylaniline, N-methylchloroaniline, N-methylbromoaniline, benzylmethylamine (BnMeNH), and the like. Preferable nucleophiles include water, methanol, ethanol, ammonia, allylamine, cyclohexylamine, and benzylamine.

These nucleophiles can be added to the solution either before or after oxidation, so that the one-pot procedure may proceed continuously without isolating the intermediates to obtain the corresponding products, 3-pyrrolidinols. In the case of preparing 3,4-epoxypyrrolidines having formula (2), these nucleophiles are not necessary, and can be used as inactive solvents by controlling the reaction temperature.

If desired, the oxidation of 3-pyrrolines having formula (3) may be accelerated using ultraviolet light. Lamps with wave length from the ultraviolet to the visible light range (200 nm–400 nm) can be selected for the irradiation of 3-pyrrolines. For example, such lamps include an Argon Resonance Lamp, a Flash UV (Ultra Violet) Lamp, an Ultra High Pressure Hg (mercury) Lamp, a High Pressure Hg (mercury) Lamp, a Low Pressure Hg (mercury) Lamp, a Deuterium Lamp, a Xe (xenon) Lamp, a W (tungsten) Lamp, a Metal Halide Lamp, and the like. In particular, a High Pressure Hg (mercury) Lamp and a Xe (xenon) Lamp are preferable.

Although the use of these lamps is able to accelerate oxidation of 3-pyrrolines having formula (3), the reaction system can be changed freely by changing the irradiation time, the irradiation strength or by omitting the irradiation.

The reaction solvents may be freely selected in the oxidation process. For example, suitable reaction solvents include, but are not limited to, water, methanol, ethanol, propanol, acetone, methylethylkotone, methylisobutylketone, ethyl acetate, methyl propionate, hexane, cyclohexane, benzene, toluene, chloroform, dichloromethane, dichloroethane, tetrahydrofuran, diethyl ether, diisopropyl ether, ethylene glycol, diethylene glycol, and the like. Either only one kind of solvent may be used, or mixtures of solvents may be used. Alternatively, the solvents can be omitted. With regard to combining the above solvents with the nucleophiles from which substituent group Nu in formula (1) derives, they can be made active and/or inactive by controlling the reaction temperature.

The reaction temperature will depend on the time required for completing the oxidation. In general, the reaction may be conducted at about 0–100° C. In particular, the reaction temperature is about 0–30° C. for obtaining 3,4-epoxypyrrolidines and is about 30–100° C. for obtaining 3-pyrrolidinols.

3-pyrrolines having formula (3) may be produced by reacting cis-2-butene derivatives having formula (7) with at least one primary amine having formula (8). This reaction allows cyclization of cis-2-butene derivatives of formula (7) and the formnation of 3-pyrrolines of formula (3). Cis-2-butene derivatives of formula (7) may be produced from cis-2-butene-1,4-diols of formula (9) by reacting the cis-2-butene-1,4-diols of formula (9) with a halogenation reagent in the presence of at least one base.

The substituent groups $R^{10}$ in the primary amines of formula (8):

$$R^{10}-NH_2 \qquad (8)$$

which are used for preparing 3-pyrrolines, include, but are not limited to, alkyl groups, such as methyl, ethyl, n-, iso-propyl, n-, i-, t-butyl, trifluoromethyl, and the like; cycloalkyl groups, such as cyclohexyl and the like; alkenyl groups, such as vinyl, allyl, methallyl, homoallyl, and the like; aryl groups, such as phenyl, fluorophenyl, difluorophenyl, trifluorophenyl, chlorophenyl, dichlorophenyl, trichlorophenyl, bromophenyl, dibromophenyl, tribromophenyl, nitrophenyl, dinitrophenyl, trinitrophenyl, cyanophenyl, dicyanophenyl, tricyanophenyl, tolyl, dimethylphenyl, trimethylphenyl, trifluoromethylphenyl, naphthyl, and the like; and alalkyl groups, such as benzyl, phenylethyl, phenethyl, naphthylmethyl, 1-, 2-phenylvinyl, and the like.

Primary amines include, but are not limited to, methylamine, ethylamine, n-, i-propylamine, n-, i-, t-butylamine, cyclohexylamine, allylamine, allylamine, homoallylamine, benzylamine, aniline, chloroaniline, bromoaniline, toluidine and the like. Of the suitable primary amines, cyclohexylamine, benzylamine, and aniline are preferable. Suitable amounts of amines are in the range of about 3.0–5.0 moles amines to 1.0 mole of cis-2-butene derivatives having formula (7) and can be preferably used efficiently and economically.

Bases used for preparing cis-2-butene derivatives of formula (7) from cis-2-butene-1,4-diols of formula (9), can be selected freely unless these would react with the starting materials. Formula (7) is represented by:

wherein $R^8$ and $R^9$ are independently hydrogen (H) or a $C_1-C_{10}$ alkyl group, a cycloalkyl group, an aryl group, or an aralkyl group which can be optionally substituted, $A^1$ and $A^2$ are independently halogens or sulfonyloxy groups. Formula (9) is represented by:

wherein $R^{11}$ and $R^{12}$ are independently hydrogen (H) or a $C_1-C_{10}$ alkyl group, a cycloalkyl group, an aryl group, an alalkyl group which can be optionally substituted. Tertiary amines are the preferred bases. Tertiary amines include, but are not limited to, triethylamine, tripropylamine, tributylamine, tribenzylamine, N, N'-dimethylaniline, N, N'-dimethyltoluidine, pyridine, 4-(N, N'-dimethylamino) pyridine, and the like. Preferably, the amount of bases used is in the range of about 2.0–3.0 moles of base to 1.0 mole of cis-2-butene-1,4-diols of formula (9). More preferably the amount of base used is in the range of about 2.0–2.2 moles of base and can be used efficiently and economically.

The substituent group, $A^3$, in the sulfonyl halides of formula (10) which are used as halogenation reagents in the first process include halogens such as Cl, Br, and I. Formula (10) is represented by:

$$R^{13}SO_2A^3 \quad (10)$$

wherein $R^{13}$ represents a $C_1$–$C_{10}$ alkyl group, a cycloalkyl group, an aryl group, or an aralkyl group optionally substituted; and $A^3$ is a halogen. In particular, sulfonyl chlorides are preferable.

The substituent groups $R^{13}$ in the sulfonyl halides, which are used for preparing cis-2-butene derivatives of formula (7) or 3-pyrrolines of formula (3), include, but are not limited to alkyl groups, such as methyl, ethyl, n-, iso-propyl, n-, i-, t-butyl, trifluoromethyl, and the like; cycloalkyl groups, such as cyclohexyl and the like; alkenyl groups, such as vinyl, allyl, methallyl, homoallyl, and the like; aryl groups, such as phenyl, fluorophenyl, difluorophenyl, trifluorophenyl, chlorophenyl, dichlorophenyl, trichlorophenyl, bromophenyl, dibromophenyl, tribromophenyl, nitrophenyl, dinitrophenyl, trinitrophenyl, cyanophenyl, dicyanophenyl, tricyanophenyl, tolyl, dimethylphenyl, trimethylphenyl, trifluoromethylphenyl, naphthyl, and the like; and aralkyl groups, such as benzyl, phenylethyl, phenethyl, naphthylmethyl, 1-, 2-phenylvinyl, and the like.

The sulfonyl chlorides include, but are not limited to, methanesulfonyl chloride, ethanesulfonyl chloride, n-, i-propanesulfonyl chloride, n-, i-, t-butanesulfonyl chloride, cyclohexanesulfonyl chloride, trifluoromethanesulfonyl chloride, benzenesulfonyl chloride, o-, m-, p-chlorobenzenesulfonyl chloride, o-, m-, p-toluenesulfonyl chloride, naphthalenesulfonyl chloride, benzylsulfonyl chloride, and the like. Of the suitable sulfonyl chlorides, methanesulfonyl chloride, benzenesulfonyl chloride, and p-toluenesulfonyl chloride are preferable.

The amount of sulfonyl halides used is in the range of about 2.0–3.0 moles of base to 1.0 mole cis-2-butene-1,4-diols of formula (9). Preferably, the amount is about 2.0–2.2 moles of sulfonyl halides is used for efficiency and economy.

In the case where the following two processes:

(A) derivation of cis-2-butene compounds from cis-2-butene-1,4-diols having formula (9) and (B) cyclization between cis-2-butene derivatives of formula (7) and primary amines of formula (8)

are performed in a continuous process, without isolating cis-2-butene derivatives about 2.0 moles of sulfonyl halides is preferably used to prevent side reactions between excess sulfonyl halides and primary amines.

Reaction solvents may be selected freely in the preparation process of cis-2-butene derivatives or 3-pyrrolines. For example, acetone, methylethylketone, methylisobutylketone, ethyl acetate, methyl propionate, hexane, cyclohexane, benzene, toluene, chloroform, dichloromethane, dichloroethane, carbon tetrachloride, tetrahydrofuran, diethyl ether, diisopropyl ether, and the like are suitable reaction solvents. Either one kind of solvent, mixtures thereof, or no solvents can be used.

In the case where the two processes (A) and (B) are continuously conducted without isolating cis-2-butene derivatives of formula (7), the same solvent can be used through several processes.

The temperature depends on the time for completing this cyclization reaction. Generally, the temperature is about 0 to 15° C. when sulfonyl halides of formula (10) are added to the reaction mixture. Following addition of the sulfonyl halides, the reaction may be performed at about ambient temperature to 60° C. with stirring of the solution. Although the temperature in the second stage depends on the reactivity of primary amines of formula (8), the temperature range may be about room temperature to about 100° C.

With regard to the operation of reaction mixture after completion and the isolation of products, the two processes of the previous stage can be conducted to the next stage continuously without isolating intermediates. If one needs to isolate the products (intermediates), one has only to conduct simple operations such as filtration, extraction, and so on. "Conducting the two processes of the previous stage to the next stage continuously without isolating intermediates" refers to a one-pot reaction, advancing to the next reaction without transferring the solution to the another reactor. For example, if the cis-2-butene derivative solution contains the following compounds,

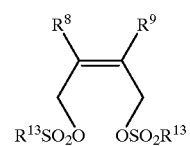

[Formula (12)]

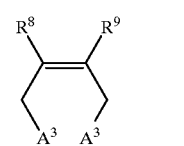

[Formula (13)]

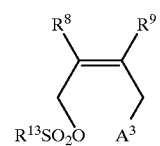

[Formula (14)]

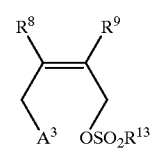

[Formula (15)]

wherein $R^8$ and $R^9$ are independently hydrogen (H) or a $C_1$–$C_{10}$ alkyl group, a cycloalkyl group, an aryl group, or an aralkyl group which can be optionally substituted; $R^{13}$ represents a $C_1$–$C_{10}$ alkyl group, a cycloalkyl group, an aryl group, an aralkyl group optionally substituted; and $A^3$ is a halogen, or if the oxidation solution contains the following two compounds:

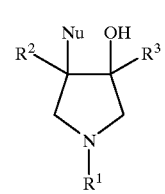

[Formula (1)]

-continued

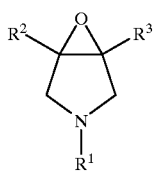

[Formula (2)]

wherein $R^1$ is hydrogen (H), a halogen, a cyano group (CN), a nitro group ($NO_2$), a hydroxyl group (OH), an alkoxyl group (OR), a carboxyl group ($CO_2H$), an alkoxycarbonyl group ($CO_2R$), an acyl group (COR), a carbomyl group ($H_2NCO$), a sulfide group (SH, or SR), a sulfinyl group (SOR), a sulfonyl group ($SO_2R$), a sulfamide group ($SO_2NRR'$), or a $C_1$–$C_{10}$ alkyl group, cycloalkyl group, aryl group, alalkyl group, optionally substituted; $R^2$ and $R^3$ each independently represent a $C_1$–$C_{10}$ alkyl group, cycloalkyl group, aryl group, or alalkyl group, optionally substituted, and Nu is a hydroxyl group (OH), alkoxyl group (OR), or amino group (NRR') optionally substituted, we can conduct the solution to the next stage continuously without isolating intermediates.

Processing after continuous reaction only involves simple operations such as filtration, extraction, and so on. For example, the following methods may be freely selected: (1) after direct addition and reaction of primary amines to the solution Process (A), both tertiary amine salts and primary amine salts are removed; (2) after removing tertiary amine salts from the solution Process (A), the addition and reaction of primary amines is performed followed by removal of primary amine salts.

EXAMPLES

The following examples are illustrative of the invention and are not to be construed in any way to limit the scope of the invention, which is defined in the appended claims.

Example 1

Preparation of the cis-2-butene Derivative

In a round-flask reactor containing a solution of 35.4 g (0.4 mol) of cis-2-butene-1,4-diol, 83.8 g (0.8 mol) of triethylamine, and 416.6 g of ethyl acetate, methanesulfonyl chloride was added dropwise with stirring for 30 min. at about 5° C. using an ice-bath. After 2 hours of stirring, the crystallized solid was removed by filtration, and the solvent was evaporated under reduced pressure. 60.0 g of residue was obtained, of which the ratio of cis-1,4-dichloro-2-butene:cis-4-chloro-2-butene-1-ol methanesulfonylate:cis-2-butene-1,4-diol dimethanesulfonylate was 5:4:1.

Example 2

1-benzyl-3-pyrroline

To a solution of 60.0 g of the cis-2-butene derivative solution prepared in Example 1 and 250 g of toluene in a round flask reactor, 171.7 g (1.6 mol) of benzylamine was added dropwise with stirring for 30 min. at ambient temperature. After 2 hours of stirring, the crystallized solid was removed by filtration; 42.0 g of 35% HCl (aq) was added to the filtrate, and then excess benzylamine hydrochloride was removed by filtration or extraction. After the solvent was evaporated under reduced pressure, 57.0 g of 1-benzyl-3-pyrroline (yield 89.5%) was obtained.

Example 3

1-butyl-3-pyrroline

To a solution of 60.0 g of the cis-2-butene derivative solution prepared in Example 1 and 250 g of toluene in a round flask reactor, 117.0 g (1.6 mol) of butylamine was added dropwise with stirring for 30 min. at about 5° C. using an ice-bath. After 2 hours of stirring, the crystallized solid was removed by filtration; 42.0 g of 35% HCl (aq) was added to the filtrate, and then excess benzylamine hydrochloride was removed by filtration or extraction. After the solvent was evaporated under reduced pressure, 46.1 g of 1-butyl-3-pyrroline (yield 92.0%) was obtained.

Example 4

1-phenyl-3-pyrroline

To a solution of 60.0 g of the cis-2-butene derivative solution prepared in Example 1 and 250 g of toluene in a round flask reactor, 149.0 g (1.6 mol) of aniline was added dropwise with stirring for 30 min. at 50° C. After 2 hours of stirring, the crystallized solid was removed by filtration; 42.0 g of 35% HCl (aq) was added to the filtrate, and then excess benzylamine hydrochloride was removed by filtration or extraction. After the solvent was evaporated under reduced pressure, 52.2 g of 1-phenyl-3-pyrroline (yield 90.0%) was obtained.

Example 5

1-tolyl-3-pyrroline

To a solution of 60.0 g of the cis-2-butene derivative solution prepared in Example 1 and 250 g of toluene in a round flask reactor, 171.7 g (1.6 mol) of toluidine was added dropwise with stirring for 30 min. at 50° C. After 2 hours of stirring, the crystallized solid was removed by filtration; 42.0 g of 35% HCl (aq) was added to the filtrate, and then excess benzylamine hydrochloride was removed by filtration or extraction. After the solvent was evaporated under reduced pressure, 56.8 g of 1-tolyl-3-pyrroline (yield 89.2%) was obtained.

The results in the cyclization to 3-pyrrolines from Examples 2 to 5 are summarized in Table 1.

TABLE 1

Cyclization to 3-pyrrolines

| No. | amines | products | yields |
|---|---|---|---|
| 2 | benzylamine | 1-benzyl-3-pyrroline | 89.5% |
| 3 | n-butylamine | 1-n-butyl-3-pyrroline | 92.0% |

TABLE 1-continued

Cyclization to 3-pyrrolines

| No. | amines | products | yields |
|---|---|---|---|
| 4 |  aniline |  1-phenyl-3-pyrroline | 90.0% |
| 5 | 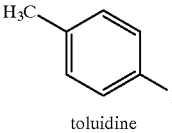 toluidine | 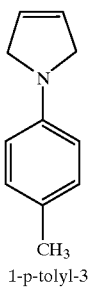 1-p-tolyl-3-pyrroline | 89.2% |

Example 6
1-benzyl-3-pyrroline (One-Pot Reaction)

To a solution containing 35.4 g (0.4 mol) of cis-2-butene-1,4-diol, 83.8 g (0.8mol) of triethylamine, and 416.6 g of ethyl acetate in a round flask reactor, methanesulfonyl chloride was added dropwise with stirring for 30 min. at about 5° C. using an ice-bath. After addition, the mixture was allowed to react with stirring for 2 hours at room temperature. To the mixture, 171.7 g (1.6 mol) of benzylamine was added continuously dropwise with stirring for 30 min. at ambient temperature. After 2 hours of stirring, the crystallized solid was removed by filtration; 42.0 g of 35% HCl (aq) was added to the filtrate, and then excess benzylamine hydrochloride was removed by filtration or extraction. After the solvent was evaporated under reduced pressure, 52.2 g of 1-benzyl-3-pyrroline (yield 82.0%) was obtained.

Example 7
1-benzyl-3-methyl-3-pyrroline (One-Pot Reaction)

To a solution containing 40.8 g (0.4 mol) of E-2-methyl-2-butene-1,4-diol, 83.8 g (0.8 mol) of triethylamine, and 416.6 g of ethyl acetate in a round flask reactor, methanesulfonyl chloride was added dropwise with stirring for 30 min. at about 5° C. using an ice-bath. After addition, the mixture was allowed to react with stirring for 2 hours at room temperature. To the mixture, 171.7 g (1.6 mol) of benzylamine was added continuously dropwise with stirring for 30 min. at ambient temperature. After 2 hours of stirring, the crystallized solid was removed by filtration; 42.0 g of 35% HCl (aq) was added to the filtrate, and then excess benzylamine hydrochloride was removed by filtration or extraction. After the solvent was evaporated under reduced pressure, 54.2 g of 1-benzyl-3-methyl-3-pyrroline (yield 78.2%) was obtained.

The results in the one-pot reaction to 3-pyrrolines from Examples 6 to 7 are summarized in Table 2.

TABLE 2

One-pot reaction from cis-2-butene-1,4-diol to 3-pyrrolines

| No. | 1,4-diols | amines | products | yields |
|---|---|---|---|---|
| 6 |  | 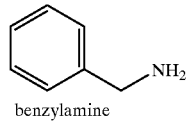 benzylamine | 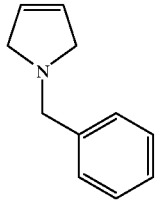 1-benzyl-3-pyrroline | 89.5% |
| 7 | 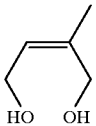 | 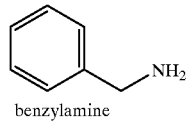 benzylamine | 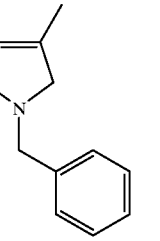 1-benzyl-3-methyl-3-pyrroline | 92.0% |

Example 8
1-benzyl-3,4-epoxypyrrolidine (Solvent:Acetone)

To a solution of 15.9 g (0.1 mol) of 1-benzyl-3-pyrroline, 12.0 g (0.12 mol) of 98% sulfuric acid, 15.0 g of water, and 60.0 g of acetone in a round flask reactor, 31.1 g (0.13 mol) of 70% m-CPBA (m-chloroperbenzoic acid produced by Tokyo Chemical Industry Co., Ltd.) was added with stirring and allowed to react for 10 hours at room temperature without irradiation by lamps. After completion, acetone was evaporated under reduced pressure, neutralized by NaOH (aq), and extracted with toluene and water. After the solvent was evaporated under reduced pressure, 17.0 g of 1-benzyl-3,4-epoxypyrrolidine (yield 97.0%) was obtained.

Example 9
1-benzyl-3,4-epoxypyrrolidine (Solvent:Methanol)

To a solution of 15.9 g (0.1 mol) of 1-benzyl-3-pyrroline, 12.0 g (0.12 mol) of 98% sulfuric acid, 15.0 g of water, and 60.0 g of methanol in a round flask reactor, 31.1 g (0.13 mol) of 70% m-CPBA (m-chloroperbenzoic acid produced by Tokyo Chemical Industry Co., Ltd.) was added with stirring and allowed to react for 10 hours at room temperature without irradiation by lamps. After completion, methanol was evaporated under reduced pressure, neutralized by NaOH (aq), and extracted with toluene and water. After the solvent was evaporated under reduced pressure, 16.9 g of 1-benzyl-3,4-epoxypyrrolidine (yield 96.7%) was obtained.

Example 10
1-benzyl-3,4-epoxypyrrolidine (Acid:methanesulfonic Acid)

To a solution of 15.9 g (0.1 mol) of 1-benzyl-3-pyrroline, 13.1 g (0.24 mol) of methanesulfonic acid (produced by Tokyo Chemical Industry Co., Ltd), 15.0 g of water, and 60.0 g of acetone in a round flask reactor, 31.1 g (0.13 mol) of 70% m-CPBA (m-chloroperbenzoic acid produced by Tokyo Chemical Industry Co., Ltd.) was added with stirring and allowed to react for 10 hours at room temperature without irradiation by lamps. After completion, acetone was evaporated under reduced pressure, neutralized by NaOH (aq), and extracted with toluene and water. After the solvent was evaporated under reduced pressure, 16.6 g of 1-benzyl-3,4-epoxypyrrolidine (yield 94.7%) was obtained.

Example 11
1-benzyl-3,4-epoxypyrrolidine (Acid:p-chlorobenzenesulfonic Acid)

To a solution of 15.9 g (0.1 mol) of 1-benzyl-3-pyrroline, 46.2 g (0.24 mol) of p-chlorobenzenesulfonic acid (produced by Tokyo Chemical Industry Co., Ltd.), 15.0 g of water, and 60.0 g of acetone in a round flask reactor, 31.1 g (0.13 mol) of 70% m-CPBA (m-chloroperbenzoic acid produced by Tokyo Chemical Industry Co., Ltd.) was added with stirring and allowed to react for 10 hours at room temperature without irradiation by lamps. After completion, acetone was evaporated under reduced pressure, neutralized by NaOH (aq), and extracted with toluene and water. After the solvent was evaporated under reduced pressure, 16.8 g of 1-benzyl-3,4-epoxypyrrolidine (yield 95.9%) was obtained.

Example 12
1-benzyl-3,4-epoxypyrrolidine (Acid:2-mesitylenesulfonic Acid dihydrate)

To a solution of 15.9 g (0.1 mol) of 1-benzyl-3-pyrroline, 56.7 g (0.24 mol) of 2-mesitylenesulfonic acid dihydrate (produced by Aldrich Chemical Co., Inc.), 15.0 g of water, and 60.0 g of acetone in a round flask reactor, 31.1 g (0.13 mol) of 70% m-CPBA (m-chloroperbenzoic acid produced by Tokyo Chemical Industry Co., Ltd.) was added with stirring and allowed to react for 10 hours at room temperature without irradiation by lamps. After completion, acetone was evaporated under reduced pressure, neutralized by NaOH (aq), and extracted with toluene and water. After the solvent was evaporated under reduced pressure, 16.6 g of 1-benzyl-3,4-epoxypyrrolidine (yield 94.7%) was obtained.

Example 13
1-benzyl-3,4-epoxypyrrolidine (Irradiation Condition)

To a solution of 15.9 g (0.1 mol) of 1-benzyl-3-pyrroline, 12.0 g (0.12 mol) of 98% sulfuric acid, 15.0 g of water, and 60.0 g of acetone in a Pyrex round flask reactor, 45.6 g (0.20 mol) of $(NH_4)_2S_2O_8$ (ammonium peroxydisulfate produced by Mitsubishi Gas Chemical Industry Co., Ltd.) was added with stirring and allowed to react for 10 hours at room temperature with irradiation by 500 W Xe lamps (UXL-500D xenon lamp produced by Ushio). After completion, acetone was evaporated under reduced pressure, neutralized by NaOH (aq), and extracted with toluene and water. After the solvent was evaporated under reduced pressure, 4.9 g of 1-benzyl-3,4-epoxypyrrolidine (yield 28.0%) was obtained and 11.9 g (yield 75.0%) of 1-benzyl-3-pyrroline was recovered.

Example 14
1-benzyl-3,4-epoxypyrrolidine (Irradiation Condition)

To a solution of 15.9 g (0.1 mol) of 1-benzyl-3-pyrroline, 12.0 g (0.12 mol) of 98% sulfuric acid, 15.0 g of water, and 60.0 g of acetone in a Pyrex round flask reactor, 47.6 g (0.20 mol) of $Na_2S_2O_8$ (sodium peroxydisulfate produced by Mitsubishi Gas Chemical Industry Co., Ltd.) was added with stirring and allowed to react for 10 hours at room temperature with irradiation by 500 W Xe lamps (UXL-500D xenon lamp produced by Ushio). After completion, acetone was evaporated under reduced pressure, neutralized by NaOH (aq), and extracted with toluene and water. After the solvent was evaporated under reduced pressure, 4.5 g of 1-benzyl-3,4-epoxypyrrolidine (yield 23.3%) was obtained and 11.9 g (yield 75.0%) of 1-benzyl-3-pyrroline was recovered.

Example 15
1-benzyl-3,4-epoxypyrrolidine (Irradiation Condition)

To a solution of 15.9 g (0.1 mol) of 1-benzyl-3-pyrroline, 12.0 g (0.12 mol) of 98% sulfuric acid, 15.0 g of water, and 60.0 g of acetone in a quartz round flask reactor, 45.6 g (0.20 mol) of $(NH_4)_2S_2O_8$ (ammonium peroxydisulfate produced by Mitsubishi Gas Chemical Industry Co., Ltd.) was added with stirring and allowed to react for 10 hours at room temperature with irradiation by 500 W Xe lamps (UXL-500D xenon lamp produced by Ushio). After completion, acetone was evaporated under reduced pressure, neutralized by NaOH (aq), and extracted with toluene and water. After the solvent was evaporated under reduced pressure, 10.5 g of 1-benzyl-3,4-epoxypyrrolidine (yield 54.4%) was obtained and 6.4 g (yield 40.0%) of 1-benzyl-3-pyrroline was recovered.

Example 16
1-benzyl-3,4-epoxypyrrolidine (Irradiation Condition)

To a solution of 15.9 g (0.1 mol) of 1-benzyl-3-pyrroline, 12.0 g (0.12 mol) of 98% sulfuric acid, 15.0 g of water, and 60.0 g of acetone in a quartz round flask reactor, 45.6 g (0.20 mol) of $(NH_4)_2S_2O_8$ (ammonium peroxydisulfate produced by Mitsubishi Gas Chemical Industry Co., Ltd.) was added with stirring and allowed to react for 5 days at room temperature with irradiation by 500 W Xe lamps (UXL-500D xenon lamp produced by Ushio). After completion, acetone was evaporated under reduced pressure, neutralized by NaOH (aq), extracted with toluene and water. After the solvent was evaporated under reduced pressure, 16.6 g of 1-benzyl-3,4-epoxypyrrolidine (yield 94.7%) was obtained and 1-benzyl-3-pyrroline was not recovered.

The results in the epoxidation to 1-benzyl-3,4-epoxypyrrolidine from Examples 8 to 16 are summarized in Table 3.

TABLE 3

Epoxidation of 1-benzyl-3-pyrroline to 1-benzyl-3,4-epoxypyrrolidine

| No. | acids | oxidants | solvents | time, temp. | irradiation condition | yields (recovered) |
|---|---|---|---|---|---|---|
| 8 | 98% $H_2SO_4$ | m-CPBA | acetone | 10 h, r. t. | none | 97.0% |
| 9 | 98% $H_2SO_4$ | m-CPBA | MeOH | 10 h, r. t. | none | 96.7% |
| 10 | $CH_3SO_3H$ | m-CPBA | acetone | 10 h, r. t. | none | 94.7% |
| 11 | 4-chlorobenzenesulfonic acid (Cl-C$_6$H$_4$-SO$_3$H) | m-CPBA | acetone | 10 h, r. t. | none | 95.9% |
| 12 | 2-mesitylenesulfonic acid (2,4,6-(CH$_3$)$_3$C$_6$H$_2$-SO$_3$H) | m-CPBA | acetone | 10 h, r. t. | none | 94.7% |
| 13 | 98% $H_2SO_4$ | $(NH_4)_2S_2O_8$ | acetone | 10 h, r. t. | Pyrex 500W Xe | 28.0% (75.0%) |
| 14 | 98% $H_2SO_4$ | $Na_2S_2O_8$ | acetone | 10 h, r. t. | Pyrex 500W Xe | 23.3% (75.0%) |
| 15 | 98% $H_2SO_4$ | $(NH_4)_2S_2O_8$ | acetone | 10 h, r. t. | quartz 500W Xe | 54.4% (40.0%) |
| 16 | 98% $H_2SO_4$ | $(NH_4)_2S_2O_8$ | acetone | 5 d, r. t. | quartz 500W Xe | 94.7% |

Example 17

1-benzyl-3,4-dihydroxypyrrolidine

To a solution of 15.9 g (0.1 mol) of 1-benzyl-3-pyrroline, 12.0 g (0.12 mol) of 98% sulfuric acid, 15.0 g of water, and 60.0 g of acetone in a round flask reactor, 31.1 g (0.13 mol) of 70% m-CPBA (m-chloroperbenzoic acid produced by Tokyo Chemical Industry Co., Ltd.) was added with stirring and allowed to react for 10 hours at 40° C. without irradiation by lamps. After completion, acetone was evaporated under reduced pressure, neutralized by NaOH (aq), and extracted with toluene and water. After the solvent was evaporated under reduced pressure, 17.4 g of 1-benzyl-3,4-dihydroxypyrrolidine (yield 90.0%) was obtained.

Example 18

1-benzyl-3,4-dihydroxypyrrolidine (Acid:methanesulfonic Acid)

To a solution of 15.9 g (0.1 mol) of 1-benzyl-3-pyrroline, 13.1 g (0.24 mol) of methanesulfonic acid (produced by Tokyo Chemical Industry Co., Ltd.), 15.0 g of water, and 60.0 g of acetone in a round flask reactor, 31.1 g (0.13 mol) of 70% m-CPBA (m-chloroperbenzoic acid produced by Tokyo Chemical Industry Co., Ltd.) was added with stirring and allowed to react for 10 hours at 40° C. without irradiation by lamps. After completion, acetone was evaporated under reduced pressure, neutralized by NaOH (aq), and extracted with toluene and water. And then after the solvent was evaporated under reduced pressure, 16.6 g of 1-benzyl-3,4-dihydroxypyrrolidine (yield 85.9%) was obtained.

Example 19

1-benzyl-3,4-dihydroxypyrrolidine (Acid:p-chlorobenzenesulfonic Acid)

To a solution of 15.9 g (0.1 mol) of 1-benzyl-3-pyrroline, 46.2 g (0.24 mol) of p-chlorobenzenesulfonic acid (produced by Tokyo Chemical Industry Co., Ltd.), 15.0 g of water, and 60.0 g of acetone in a round flask reactor, 31.1 g (0.13 mol) of 70% m-CPBA (m-chloroperbenzoic acid produced by Tokyo Chemical Industry Co., Ltd.) was added with stirring and allowed to react for 10 hours at 40° C. without irradiation by lamps. After completion, acetone was evaporated under reduced pressure, neutralized by NaOH (aq), and extracted with toluene and water. After the solvent was evaporated under reduced pressure, 16.8 g of 1-benzyl-3,4-dihydroxypyrrolidine (yield 86.9%) was obtained.

Example 20

1-benzyl-3,4-dihydroxypyrrolidine (acid:2-mesitylenesulfonic Acid dihydrate)

To a solution of 15.9 g (0.1 mol) of 1-benzyl-3-pyrroline, 56.7 g (0.24 mol) of 2-mesitylenesulfonic acid dihydrate (produced by Aldrich Chemical Co., Inc.), 15.0 g of water, and 60.0 g of acetone in a round flask reactor, 31.1 g (0.13 mol) of 70% m-CPBA (m-chloroperbenzoic acid produced by Tokyo Chemical Industry Co., Ltd.) was added with stirring and allowed to react for 10 hours at 40° C. without irradiation by lamps. After completion, acetone was evaporated under reduced pressure, neutralized by NaOH (aq), and extracted with toluene and water. After the solvent was evaporated under reduced pressure, 16.6 g of 1-benzyl-3,4-dihydroxypyrrolidine (yield 85.9%) was obtained.

Example 21

1-benzyl-3,4-dihydroxypyrrolidine (Irradiation Condition)

To the solution of 15.9 g (0.1 mol) of 1-benzyl-3-pyrroline, 12.0 g (0.12 mol) of 98% sulfuric acid, 15.0 g of water, and 60.0 g of acetone in a quartz round flask reactor, 45.6 g (0.20 mol) of $(NH_4)_2S_2O_8$ (ammonium peroxydisulfate produced by Mitsubishi Gas Chemical Industry Co., Ltd.) was added with stirring and allowed to react for 5 days at ambient temperature with irradiation by 500 W Xe lamps (UXL-500D xenon lamp produced by Ushio). After completion, acetone was evaporated under reduced pressure, neutralized by NaOH (aq), and extracted with toluene and water. After the solvent was evaporated under reduced pressure, 17.4 g of 1-benzyl-3,4-dihydroxypyrrolidine (yield 90.0%) was obtained and 1-benzyl-3-pyrroline was not recovered.

The results in the one-pot reaction to 1-benzyl-3,4-dihydroxypyrrolidine from Examples 17 to 21 are summarized in Table 4.

TABLE 4

One-pot reaction from 1-benzyl-3-pyrroline to 1-benzyl-3,4-dihydroxypyrrolidine

| No. | acids | oxidants | solvents | time, temp. | irradiation condition | yields |
|---|---|---|---|---|---|---|
| 17 | 98% $H_2SO_4$ | m-CPBA | acetone | 10 h, 40° C. | none | 90.0% |
| 18 | $CH_3SO_3H$ | m-CPBA | acetone | 10 h, 40° C. | none | 85.9% |
| 19 | Cl-C$_6$H$_4$-SO$_3$H | m-CPBA | acetone | 10 h, 40° C. | none | 86.9% |
| 20 | 2,4,6-(CH$_3$)$_3$C$_6$H$_2$-SO$_3$H | m-CPBA | acetone | 10 h, 40° C. | none | 85.9% |
| 21 | 98% $H_2SO_4$ | $(NH_4)_2S_2O_8$ | acetone | 5 d, 40° C. | quartz 500W Xe | 90.0% |

Example 22

1-benzyl-4-methoxy-3-pyrrolidinol (Irradiation Condition)

To a solution of 15.9 g (0.1 mol) of 1-benzyl-3-pyrroline, 12.0 g (0.12 mol) of 98% sulfuric acid, and 60.0 g of acetone in a quartz round flask reactor, 45.6 g (0.20 mol) of $(NH_4)_2S_2O_8$ (ammonium peroxydisulfate produced by Mitsubishi Gas Chemical Industry Co., Ltd.) was added with stirring and allowed to react for 5 days at room temperature with irradiation by 500 W Xe lamps (UXL-500D xenon lamp produced by Ushio). 57.9 g (0.3 mol) of 28wt % NaOMe in methanol solution (produced by Katayama Chemical Industry Co., Ltd.) was continuously added to the reaction mixture and stirred for 5 hours under reflux. After completion, acetone and methanol were evaporated under reduced pressure, and extracted with toluene and water. After the solvent was evaporated under reduced pressure, 15.8 g of 1-benzyl-4-methoxy-3-pyrrolidinol (yield 76.0%) was obtained.

Example 23

1-benzyl-4-benzylamino-3-pyrrolidinol (Irradiation Condition)

To a solution of 15.9 g (0.1 mol) of 1-benzyl-3-pyrroline, 12.0 g (0.12 mol) of 98% sulfuric acid, 15.0 g of water, and 60.0 g of acetone in a quartz round flask reactor, 45.6 g (0.20 mol) of $(NH_4)_2S_2O_8$ (ammonium peroxydisulfate produced by Mitsubishi Gas Chemical Industry Co., Ltd.) was added with stirring and allowed to react for 5 days at room temperature with irradiation by 500 W Xe lamps (UXL-500D xenon lamp produced by Ushio). After evaporation of acetone under reduced pressure, continuously 32.1 g (0.3 mol) of benzylamine (produced by Katayama Chemical Industry Co., Ltd.) was added to the reaction mixture and stirred for 5 hours at 100° C. After completion, excess benzylamine was removed by distillation under reduced pressure, and extracted with toluene and water. After the solvent was evaporated under reduced pressure, 20.9 g of 1-benzyl-4-benzylamino-3-pyrrolidinol (yield 74.0%) was obtained.

Example 24

1-benzyl-4-diethylamino-3-pyrrolidinol (Irradiation Condition)

To a solution of 15.9 g (0.1 mol) of 1-benzyl-3-pyrroline, 12.0 g (0.12 mol) of 98% sulfuric acid, 15.0 g of water, and 60.0 g of acetone in a quartz round flask reactor, 45.6 g (0.20 mol) of $(NH_4)_2S_2O_8$ (ammonium peroxydisulfate produced by Mitsubishi Gas Chemical Industry Co., Ltd.) was added with stirring and allowed to react for 5 days at room temperature with irradiation by 500 W Xe lamps (UXL-500D xenon lamp produced by Ushio). 21.9 g (0.3 mol) of diethylamine (produced by Katayama Chemical Industry Co., Ltd.) was continuously added to the reaction mixture and stirred for 5 hours under reflux. After completion, acetone and excess diethylamine were evaporated under reduced pressure, and extracted with toluene and water. After the solvent was evaporated under reduced pressure, 18.4 g of 1-benzyl-4-diethylamino-3-pyrrolidinol (yield 73.9%) was obtained.

Example 25

1-benzyl-4-phenylthio-3-pyrrolidinol (Irradiation Condition)

To a solution of 15.9 g (0.1 mol) of 1-benzyl-3-pyrroline, 12.0 g (0.12 mol) of 98% sulfuric acid, 15.0 g of water, and 60.0 g of acetone in a quartz round flask reactor, 45.6 g (0.20 mol) of $(NE_4)_2S_2O_8$ (ammonium peroxydisulfate produced by Mitsubishi Gas Chemical Industry Co., Ltd.) was added with stirring and allowed to react for 5 days at room temperature with irradiation by 500 W Xe lamps (UXL-500D xenon lamp produced by Ushio). After evaporation of acetone under reduced pressure, continuously, 13.2 g (0.12 mol) of benzenethiol (produced by produced by Aldrich Chemical Co., Inc.) was added to the reaction mixture and stirred for 5 hours at 100° C. After completion, the reaction mixture was extracted with toluene and water. After the solvent was evaporated under reduced pressure, 20.2 g of 1-benzyl-4-phenylthio-3-pyrrolidinol (yield 70.9%) was obtained.

Example 26
1-benzyl-4-methylthio-3-pyrrolidinol (Irradiation Condition)

To a solution of 15.9 g (0.1 mol) of 1-benzyl-3-pyrroline, 12.0 g (0.12 mol) of 98% sulfuric acid, 15.0 g of water, and 60.0 g of acetone in a quartz round flask reactor, 45.6 g (0.20 mol) of $(NH_4)_2S_2O_8$ (ammonium peroxydisulfate produced by Mitsubishi Gas Chemical Industry Co., Ltd.) was added with stirring and allowed to react for 5 days at room temperature with irradiation by 500 W Xe lamps (UXL-500D xenon lamp produced by Ushio). 14.4 g (0.3 mol) of methanethiol (produced by produced by Aldrich Chemical Co., Inc.) was continuously added to the reaction mixture and stirred for 5 hours under reflux. After completion, acetone and excess diethylamine were evaporated under reduced pressure, and extracted with toluene and water. After the solvent was evaporated under reduced pressure, 14.3 g of 1-benzyl-4-methylthio-3-pyrrolidinol (yield 63.9%) was obtained.

Example 27
1-benzyl-4-methyl-3-pyrrolidinol (Irradiation Condition)

To a solution of 15.9 g (0.1 mol) of 1-benzyl-3-pyrroline, 12.0 g (0.12 mol) of 98% sulfuric acid, and 60.0 g of THF in a quartz round flask reactor, 45.6 g (0.20 mol) of $(NH_4)_2S_2O_8$ (ammonium peroxydisulfate produced by Mitsubishi Gas Chemical Industry Co., Ltd.) was added with stirring and allowed to react for 5 days at room temperature with irradiation by 500 W Xe lamps (UXL-500D xenon lamp produced by Ushio). 300 mL (0.30 mol) of 1 mol/L methyllithium (MeLi) in diethyl ether solution (produced by Kanto Chemical Co., Inc.) was continuously added to the reaction mixture and stirred for 5 hours at about 5° C. using an ice-bath. After completion, water was added to destroy excess MeLi at about 5° C. using an ice-bath. Acetone and diethyl ether were evaporated under reduced pressure, and extracted with toluene and water. After the solvent was evaporated under reduced pressure, 14.5 g of 1-benzyl-4-methyl-3-pyrrolidinol (yield 76.0%) was obtained.

Example 28
1-benzyl-4-phenyl-3-pyrrolidinol (Irradiation Condition)

To a solution of 15.9 g (0.1 mol) of 1-benzyl-3-pyrroline, 12.0 g (0.12 mol) of 98% sulfuric acid, and 60.0 g of THF in a quartz round flask reactor, 45.6 g (0.20 mol) of $(NH_4)_2S_2O_8$ (ammonium peroxydisulfate produced by Mitsubishi Gas Chemical Industry Co., Ltd.) was added with stirring and allowed to react for 5 days at room temperature with irradiation by 500 W Xe lamps (UXL-500D xenon lamp produced by Ushio). 300 mL (0.30 mol) of 1 mol/L phenyllithium (PhLi) in cyclohexane-diethyl ether solution (produced by Kanto Chemical Co., Inc.) was continuously added to the reaction mixture and stirred for 5 hours at about 5° C. using an ice-bath. After completion, water was added to destroy excess PhLi at about 5° C. using an ice-bath. Acetone and diethyl ether were evaporated under reduced pressure, and extracted with toluene and water. After the solvent was evaporated under reduced pressure, 19.3 g of 1-benzyl-4-phenyl-3-pyrrolidinol (yield 76.3%) was obtained.

The results in the one-pot reaction to 1-benzyl-3-pyrrolidinols from Examples 21 to 28 are summarized in Table 5.

TABLE 5

One-pot reaction from 1-benzyl-3-pyrroline to 1-benzyl-3-pyrrolidinols

| No. | acids | oxidants | nucleophiles | products | yields |
|---|---|---|---|---|---|
| 21 | 98% $H_2SO_4$ | $(NH_4)_2S_2O_8$ | $H_2O$ | 1-benzyl-3,4-dihydroxy-pyrrolidine | 90.0% |
| 22 | 98% $H_2SO_4$ | $(NH_4)_2S_2O_8$ | NaOMe | 1-benzyl-4-methoxy-3-pyrrolidinol | 76.0% |
| 23 | 98% $H_2SO_4$ | $(NH_4)_2S_2O_8$ | $PhCH_2NH_2$ | 1-benzyl-4-benzylamino-3-pyrrolidinol | 74.0% |
| 24 | 98% $H_2SO_4$ | $(NH_4)_2S_2O_8$ | $Et_2NH$ | 1-benzyl-4-diethylamino-3-pyrrolidinol | 73.9% |
| 25 | 98% $H_2SO_4$ | $(NH_4)_2S_2O_8$ | PhSH | 1-benzyl-4-phenylthio-3-pyrrolidinol | 70.9% |
| 26 | 98% $H_2SO_4$ | $(NH_4)_2S_2O_8$ | MeSH | 1-benzyl-4-methylthio-3-pyrrolidinol | 63.9% |
| 27 | 98% $H_2SO_4$ | $(NH_4)_2S_2O_8$ | MeLi | 1-benzyl-4-methyl-3-pyrrolidinol | 76.0% |
| 28 | 98% $H_2SO_4$ | $(NH_4)_2S_2O_8$ | PhLi | 1-benzyl-4-phenyl-3-pyrrolidinol | 76.3% |

What is claimed is:

1. A method for producing an epoxypyrrolidine of formula (2)

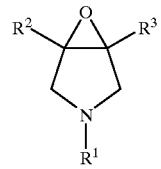

(2)

wherein $R^1$ is hydrogen, a halogen, a cyano group, a nitro group, a hydroxyl group, an alkoxyl group, a carboxyl group, an alkoxycarbonyl group, an acyl group, a carbamoyl group, a sulfide group, a sulfinyl group, a sulfonyl group, a sulfamide group, or a $C_1$–$C_{10}$ alkyl group, a cycloalkyl group, an aryl group, or an aralkyl group optionally substituted; $R^2$ and $R^3$ each independently represent a $C_1$–$C_{10}$ alkyl group, a cycloalkyl group, an aryl group, or aralkyl group, optionally substituted; by oxidizing a compound of formula (3) wherein formula (3) is:

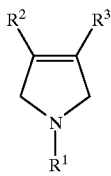
(3)

wherein $R^1$ is hydrogen, a halogen, a cyano group, a nitro group, a hydroxyl group, an alkoxyl group, a carboxyl group, an alkoxycarbonyl group, an acyl group, a carbamoyl group, a sulfide group, a sulfinyl group, a sulfonyl group, a sulfamide group, or a $C_1$–$C_{10}$ alkyl group, a cycloalkyl group, an aryl group, an aralkyl group optionally substituted; $R^2$ and $R^3$ each independently represent a $C_1$–$C_{10}$ alkyl group, an cycloalkyl group, an aryl group, an aralkyl group, optionally substituted;

the step which comprises oxidizing a compound of formula (3) with a peroxide in the presence of an acidic medium wherein said peroxide is selected from the group consisting of peroxymonosulfuric acids, peroxymonosulfates of formula (4):

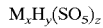
(4)

wherein M repersents alkali metals, alkaline earth metals, elements of group 3A in the periodic table, or ammonium groups of formula (6); and each of x, y, and z represents integers from 0–3 provided the relation x+y=2z is satisfied, and peroxydisulfuric acids and peroxydisulfates of formula (5):

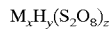
(5)

wherein M represents alkali metals, alkaline earth metals, elements of group 3A in the periodic table, or ammonium groups having formula (6):

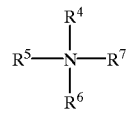
(6)

wherein $R^4$, $R^5$, $R^6$ and $R^7$ each independently represent hydrogen, a $C_1$–$C_{10}$ alkyl group, a cycloalkyl group, an aryl group, or an aralkyl group, and each of x, y and z represents integers from 0–3 provided, the relation x+y=2z is satisfied.

2. The method according to claim 1 wherein said pyrrolidine derivative is a 3,4-epoxypyrrolidine of formula (2) produced at a temperature of about 0 to 30° C.

3. The method of claim 1 wherein said 3-pyrrolines are oxidized with peroxides in the presence of said acid by photo-irradiation.

* * * * *